US012697026B2

(12) United States Patent
Gray et al.

(10) Patent No.: US 12,697,026 B2
(45) Date of Patent: Aug. 4, 2026

(54) SYSTEM AND METHOD FOR MEASURING TILT

(71) Applicant: Lensar, Inc., Orlando, FL (US)

(72) Inventors: Gary P. Gray, Orlando, FL (US); Rudolph W. Frey, Winter Park, FL (US); Steven E. Bott, Oviedo, FL (US)

(73) Assignee: Lensar, Inc., Orlando, FL (US)

( * ) Notice: Subject to any disclaimer, the term of this patent is extended or adjusted under 35 U.S.C. 154(b) by 1124 days.

(21) Appl. No.: 17/020,549

(22) Filed: Sep. 14, 2020

(65) Prior Publication Data

US 2021/0235985 A1     Aug. 5, 2021

Related U.S. Application Data

(63) Continuation of application No. 14/728,760, filed on Jun. 2, 2015, now Pat. No. 10,772,499, which is a
(Continued)

(51) Int. Cl.
*A61B 3/107*        (2006.01)
*A61F 9/008*        (2006.01)

(52) U.S. Cl.
CPC .......... *A61B 3/107* (2013.01); *A61F 9/00827* (2013.01); *A61F 9/00838* (2013.01);
(Continued)

(58) Field of Classification Search
CPC ........ A61F 9/007; A61F 9/0079; A61F 9/008; A61F 9/00802; A61F 9/00804;
(Continued)

(56) References Cited

U.S. PATENT DOCUMENTS

| | | | |
|---|---|---|---|
| 4,538,608 A | 9/1985 | L'Esperance | |
| 4,764,930 A | 8/1988 | Bille | |

(Continued)

FOREIGN PATENT DOCUMENTS

| | | |
|---|---|---|
| WO | WO 2007/104166 | 9/2007 |
| WO | WO 2009/081286 | 7/2009 |

(Continued)

OTHER PUBLICATIONS

Jul. 23, 2010, Pentacam, Oculus:The Pentacam.
Jul. 13, 2012, WIPO, PCT/US2012/030259 Search Report.
Jul. 13, 2012, WIPO, PCT/US2012/030259 Opinion.

*Primary Examiner* — Ahmed M Farah
(74) *Attorney, Agent, or Firm* — Glen P. Belvis; Belvis Law, LLC.

(57)        ABSTRACT

A method of generating three dimensional shapes for a cornea and lens of an eye, the method including illuminating an eye with multiple sections of light and obtaining multiple sectional images of said eye based on said multiple sections of light. For each one of the obtained multiple sectional images, the following processes are performed:
  a) automatically identifying arcs, in two-dimensional space, corresponding to anterior and posterior corneal and lens surfaces of the eye by image analysis and curve fitting of the one of the obtained multiple sectional images; and
  b) determining an intersection of lines ray traced back from the identified arcs in two-dimensional space with a known position of a section of space containing the section of light that generated the one of the obtained multiple sectional images, wherein the determined intersection defines a three-dimensional arc curve. The method further including reconstructing three-dimensional shapes of the anterior and posterior cornea
(Continued)

Edge of capsule following removal of Capsulorhexis "button"

IOL haptics, used to Anchor IOL at equator of capsular bag

IOL's optic, well centered on capsulorhexis surfaces and the anterior and posterior lens surfaces based on fitting the three-dimensional arc curve to a three-dimensional shape.

12 Claims, 6 Drawing Sheets

Related U.S. Application Data continuation-in-part of application No. 14/224,012, filed on Mar. 24, 2014, now Pat. No. 10,213,340, which is a continuation of application No. 13/681, 004, filed on Nov. 19, 2012, now Pat. No. 8,708,491, said application No. 14/728,760 is a continuation of application No. 13/427,319, filed on Mar. 22, 2012, said application No. 13/681,004 is a continuation of application No. 12/509,454, filed on Jul. 25, 2009, now abandoned.

(60) Provisional application No. 61/467,601, filed on Mar. 25, 2011.

(52) U.S. Cl.
CPC .............. *A61F 2009/00844* (2013.01); *A61F 2009/0087* (2013.01); *A61F 2009/00872* (2013.01); *A61F 2009/00887* (2013.01); *A61F 2009/00889* (2013.01); *A61F 2009/00895* (2013.01)

(58) Field of Classification Search
CPC .............. A61F 9/00806; A61F 9/00825; A61F 9/00827; A61F 9/00838; A61F 2009/00842; A61F 2009/00844; A61F 2009/00861; A61F 2009/0087; A61F 2009/00872; A61F 2009/00887; A61F 2009/00889; A61F 2009/00895; A61B 3/102; A61B 3/103; A61B 3/107; A61B 3/117; A61B 3/1173
USPC ............................................. 606/4–6, 10–12
See application file for complete search history.

(56) References Cited

U.S. PATENT DOCUMENTS

| | | | |
|---|---|---|---|
| 4,901,718 A | 2/1990 | Bille | |
| 4,907,586 A | 3/1990 | Bille | |
| 5,098,426 A * | 3/1992 | Sklar | A61F 9/008 606/4 |
| 5,246,435 A | 9/1993 | Bille | |
| 5,355,181 A | 10/1994 | Ashizaki | |
| 5,439,462 A | 8/1995 | Bille | |
| 5,480,396 A | 1/1996 | Simon | |
| 5,490,849 A * | 2/1996 | Smith | G02B 19/0047 219/121.75 |
| 5,867,250 A * | 2/1999 | Baron | A61B 3/107 351/212 |
| 6,004,314 A | 12/1999 | Wei | |
| 6,099,522 A | 8/2000 | Knopp | |
| 6,197,018 B1 | 3/2001 | O'Donnell | |
| 6,312,422 B1 | 11/2001 | Dubnack | |
| 6,322,556 B1 | 11/2001 | Gwon | |
| 6,325,792 B1 | 12/2001 | Swinger | |
| 6,501,551 B1 | 12/2002 | Tearney | |
| 7,655,002 B2 | 2/2010 | Myers | |
| 8,262,646 B2 | 9/2012 | Frey | |
| 8,382,745 B2 | 2/2013 | Naranjo-Tackman | |
| 8,394,084 B2 | 3/2013 | Palankar et al. | |
| 8,403,921 B2 | 3/2013 | Palankar et al. | |
| 8,425,497 B2 | 4/2013 | Blumenkranz et al. | |
| 8,465,478 B2 | 6/2013 | Frey | |
| 8,480,659 B2 * | 7/2013 | Frey | A61F 9/00825 606/4 |
| 8,500,723 B2 | 8/2013 | Frey | |
| 8,617,146 B2 | 12/2013 | Frey | |
| 8,758,332 B2 | 6/2014 | Frey | |
| 8,801,186 B2 | 8/2014 | Frey | |
| 9,180,051 B2 | 11/2015 | Frey | |
| 9,271,645 B2 | 3/2016 | Frey | |
| 9,375,349 B2 | 6/2016 | Frey | |
| 9,545,338 B2 | 1/2017 | Frey | |
| 9,968,485 B2 | 5/2018 | Potter | |
| 10,213,340 B2 | 2/2019 | Gray | |
| 10,709,610 B2 | 7/2020 | Morley | |
| 11,090,190 B2 | 8/2021 | Morley | |
| 11,992,266 B2 * | 5/2024 | Gray | A61B 3/145 |
| 2002/0103478 A1 | 8/2002 | Gwon | |
| 2006/0195076 A1 * | 8/2006 | Blumenkranz | A61F 9/009 606/4 |
| 2007/0173794 A1 | 7/2007 | Frey | |
| 2007/0173795 A1 * | 7/2007 | Frey | A61F 9/00834 606/5 |
| 2007/0185475 A1 | 8/2007 | Frey | |
| 2008/0287928 A1 | 11/2008 | Arnoldussen | |
| 2009/0161065 A1 | 6/2009 | Smith | |
| 2010/0004641 A1 | 1/2010 | Frey | |
| 2010/0042079 A1 * | 2/2010 | Frey | A61B 3/14 606/4 |
| 2011/0028950 A1 * | 2/2011 | Raksi | A61F 9/00825 606/4 |
| 2011/0190739 A1 | 8/2011 | Frey | |
| 2012/0016350 A1 | 1/2012 | Myers | |
| 2016/0095752 A1 | 4/2016 | Srinivasan | |
| 2016/0302971 A1 | 10/2016 | Frey | |
| 2017/0290703 A1 | 10/2017 | Teuma | |
| 2018/0085256 A1 | 3/2018 | Gray | |

FOREIGN PATENT DOCUMENTS

| | | | |
|---|---|---|---|
| WO | WO 2010/109020 | 9/2010 | |
| WO | WO-2012134986 A1 * | 10/2012 | A61B 3/10 |

\* cited by examiner

Edge of capsule
following removal of
Capsulorhexis "button"

IOL haptics, used to
Anchor IOL at equator
of capsular bag

IOL's optic,
well centered on
capsulorhexis

Cornea

LRI reticule

LRI reticule

Edge of pupil

Capsulotmy
reticule

Capsulotmy reticule

Lens

Software reticule to
indicate where fragmentation
pattern should be placed

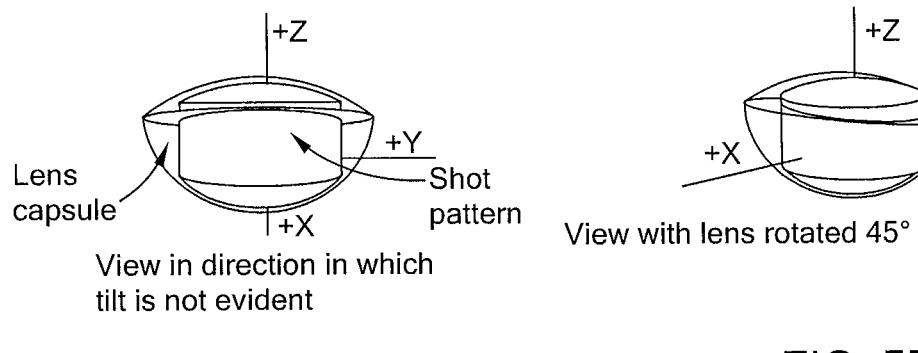
Lens capsule
Shot pattern
+Z
+Y
+X
View in direction in which
tilt is not evident
FIG. 5A
+Z
+X
+Y
View with lens rotated 45° around Z axis
FIG. 5B
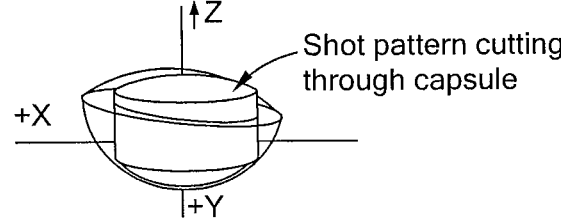
Z
Shot pattern cutting
through capsule
+X
+Y
Rotated 90° around Z axis, to show lens tilt
FIG. 5C

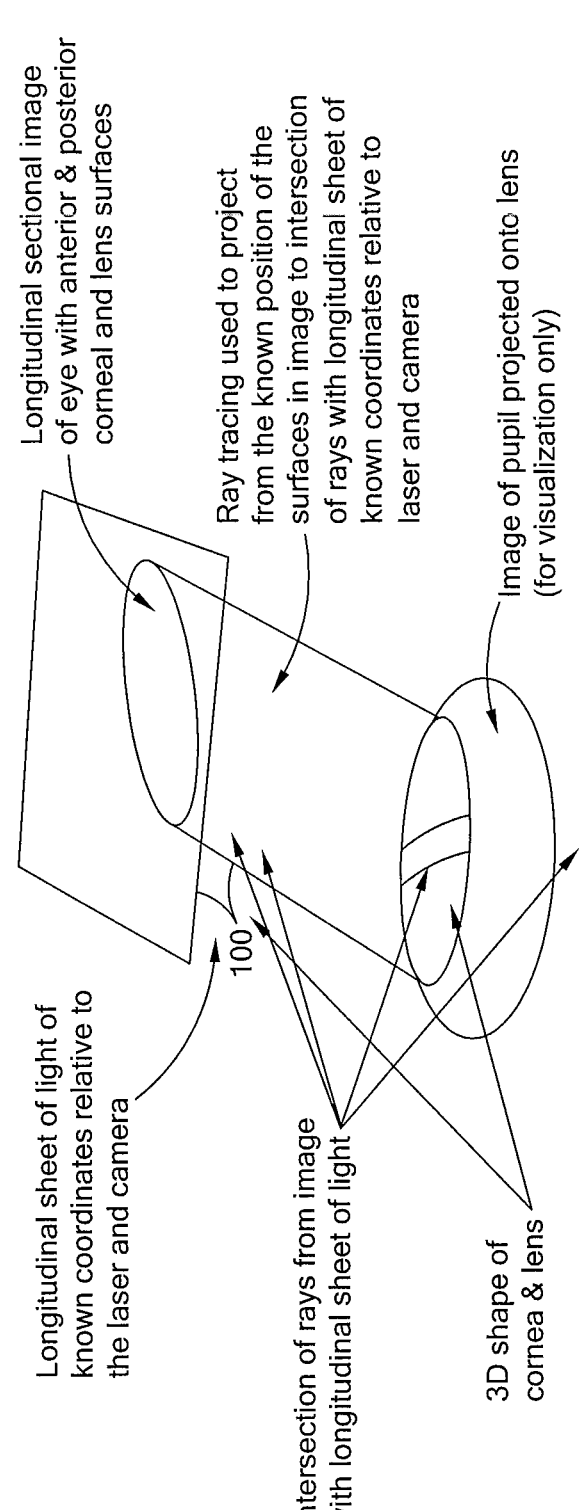

Longitudinal sectional image of eye with anterior & posterior corneal and lens surfaces Ray tracing used to project from the known position of the surfaces in image to intersection of rays with longitudinal sheet of known coordinates relative to laser and camera Image of pupil projected onto lens (for visualization only)

Longitudinal sheet of light of known coordinates relative to the laser and camera Intersection of rays from image with longitudinal sheet of light 3D shape of cornea & lens

Zernike decomposition of anterior corneal surface based on multiple longitudinal sections images Ray tracing-derived arcs on the anterior and posterior surfaces Ray tracing-derived arcs on the anterior and posterior lens

SYSTEM AND METHOD FOR MEASURING TILT

This application is a continuation of Ser. No. 14/728,760 filed Jun. 2, 2015 which is a continuation of Ser. No. 13/427,319 filed Mar. 22, 2012, which: (i) is a continuation-in-part of Ser. No. 14/224,012 filed Mar. 24, 2014, which is a continuation of Ser. No. 13/681,004 filed Nov. 19, 2012, which is a continuation of Ser. No. 12/509,454 filed Jul. 25, 2009, which claims under 35 U.S.C. § 119(e)(1) the benefit of the filing date of Jul. 25, 2008 of U.S. Provisional Application Ser. No. 61/135,190; and (ii) is a continuation of Ser. No. 13/427,319 filed Mar. 22, 2012, which claims under 35 U.S.C. § 119(e)(1) the benefit of the filing date of Mar. 25, 2011 of U.S. Provisional Application Ser. No. 61/467, 601, the entire disclosures of each of which are incorporated herein by reference.

FIELD OF THE INVENTION

The present invention relates to a method for generating three-dimensional images of a cornea and a lens of an eye and a method of surgically repairing an eye.

BACKGROUND

Obtaining the best laser phaco fragmentation results involves striking a balance between two opposing goals. The first opposing goal is to cut as much of the volume of the crystalline lens into suitable pieces as possible, particularly the cataract-hardened parts of the lens, so that as little ultrasound energy and mechanical manipulation of the lens as possible is required to remove the lens. Of necessity, this means making incisions as close as possible to the lens capsule, and particularly the posterior capsule where, for some types of cataracts, a hard, difficult-to-remove "posterior plate" resides as mentioned in 1) Kamori, K and Mochiizuki, M, J Cataract Refract Surg. Vol. 36, No. 1, January 2010, pp. 9-12 and 2) Buratto et al, "Phacoemulsification: Principles and Techniques," published by SLACK Inc., Thorofare, NJ). Cutting the posterior plate into pieces would provide a large benefit to the surgeon since it minimizes the risk of damaging the posterior capsule during the mechanical manipulation of the plate to break it into pieces or bring it into position for application of the ultrasonic phaco tip.

The second opposing goal is to have the procedure be as safe as possible by keeping a sufficient safety margin between the outermost extent of the pattern of laser incisions and the anterior and posterior capsule. The safety margin must account for all sources of error, including the most important sources of error, such as: 1) errors in measuring the positions of the anterior and posterior capsule and 2) errors in placement of laser shots by the beam guidance system.

For capsulotomies, a similar balance is required. The capsulotomy is cut as a series of stacked rings of individual laser pulses. The pulses within a ring and the z spacings between rings are spaced such that the photodisruption which occurs at each pulse has the composite effect of generating a smooth, continuous cylindrical cut. If the position of the anterior lens capsule at the desired position of the capsulotomy were known perfectly, a cylinder of very small edge height would be required; i.e., the edge height could be little more than the thickness of the lens capsule. Making the cylindrical cut with a small edge height is beneficial because it minimizes bubble formation under the lens capsule or in the anterior chamber of the eye. The formation of bubbles under the capsule can interfere with the laser cut and result in capsulotomies that are not completely cut and have residual tissue bridges between the capsulotomy "button" (circular region of anterior capsule which is removed) and the remaining lens capsule which must be manually torn. Anterior chamber bubbles can obstruct or interfere with the laser as the laser traverses the bubbles to cut parts of the cornea or lens in later parts of the laser procedure. Small edge heights for the cylindrical cut also reduce the surgery time. However, the requirement for small edge heights must be balanced against the risk that some or all of the incisions will miss the lens capsule and cut instead in the lens fibrous body or in the anterior chamber due to slight errors in the measurement of the lens capsule position or the positioning of the laser beam when making the incisions. Obviously, missing all or part of the lens capsule necessitates later manual tearing of some or all of the capsule-which negates some or all of the advantage of using the laser itself and which may also increase the risk of an anterior capsule tear when the surgeon tries to connect two parts of a laser cut with a manual tear to complete the capsulotomy.

Corneal incisions such as LRIs, as with the laser capsulotomy incisions, have stringent accuracy and precision requirements. While the arcuate incisions must cut deep into the eye (typically 90% of the 500-700u.ro thickness of the cornea), it is undesirable to cut all the way through the cornea. In addition, the amount of astigmatism correction resulting from a cut is a function of the depth of the cut.

Another factor in obtaining good clinical outcomes in cataract surgery concerns the centration of the capsulotomy. In conventional cataract surgery, the capsulorhexis is centered on the patient's dilated pupil to the best of the surgeon's ability. Note that the pupil is used for centering since the pupil is the only readily available, visible landmark available to the surgeon. After the cataractous lens has been removed, the IOL is placed into the capsule so that the IOL's optic is centered as well as possible on the capsulorhexis as shown in FIG. 1. Centering the IOL's optic on the capsulorhexis helps to prevent the IOL from tilting, relative to the axis of the eye, as the edge of the anterior lens capsule adheres to the outer part of the optic and becomes fibrotic over time. With a poorly centered IOL, the capsular edge may be partially on and partially off the IOL's optic and the fibrosis will tend to pull one side of the IOL forward more than the other side, causing the lens to tilt with a resulting increase in aberrations in the images the IOL forms on the retina.

Although the foregoing IOL centration method is widely used, it has the disadvantage that it frequently results in a shift in the optic axis of the eye following cataract surgery. The shift is due to the fact that although the optical axis of the eye generally passes close to the center of the undilated pupil, the pupil generally dilates somewhat asymmetrically and the center of the dilated pupil is decentered with respect to the undilated pupil, and thus off the optic axis as described in Merchea, et al, Invest Ophthalmol Vis Sci 2005; 46: E-Abstract 4357. The IOL, therefore, is similarly off center relative to the original optic axis of the eye, and the misalignment between the optic axis of the cornea and the optic axis of the off center IOL causes increased aberrations in the images formed by the cornea and off center IOL, thus reducing the patient's visual acuity.

In order to place laser incisions within the cornea and lens, the positions and shapes of the anterior and posterior cornea and lens surfaces need to be determined. This is accomplished in conventional laser cataract surgery by use of an imaging or biometric device built into the laser system. Most often, the device is based on OCT (Optical Coherence Tomography) as described in Maxine Lipner, "What's ahead Femto technology changing the cataract landscape", *Eye-World*, Vol. 13, No. 33, Mar. 24, 2011, p. 19 or a Scheimp-flug camera-based imaging system as disclosed in U.S. Patent Application Publication No. US 2010/0022995, the entire contents of which are incorporated herein by reference). Such systems make longitudinal sectional images of the eye; each image captures the position of the intersection of the cornea and lens with an illuminated vertical plane of light which generally passes through a diameter of the eye, i.e., includes the optic axis of the eye. The pupil position can be found from the same image, or with the assistance of a separate camera of known position and optical characteristics pointing directly into the eye. A single longitudinal sectional image may be used to allow a user of the laser to target the position of the capsulotomy and laser phaco fragmentation pattern as well as corneal incisions by using a computer mouse or other pointing device to manipulate software reticules superimposed on the longitudinal sectional image as shown in FIG. 2. This method forces the surgeon to interrupt the surgery to perform the time consuming task of manually targeting the various positions mentioned previously. The method also suffers from the lack of repeatability inherent in manual processing of images and manipulation of reticules to allow the surgeon to select the position and size of the laser phaco fragmentation pattern and capsulotomy. Since the method relies on the surgeon's skill in judging exactly where the anterior and posterior cornea and lens surfaces are within the slightly fuzzy images, it is not ideal for deciding on the optimal tradeoff between the need to cut fragmentation pattern very close to the capsule and still allowing an adequate safety margin. Furthermore, if the optic axis of the lens is tilted with respect to the axis of the laser, the tilt will be visible when a longitudinal sectional image passes through the plane defined by the axes of the laser and tilted crystalline lens, but in a longitudinal sectional image perpendicular to this plane, no tilt will be observable as will be explained in more detail below. Thus, if a laser phaco fragmentation pattern is placed on the basis of a single longitudinal sectional image, there is no way to ensure that tilt is properly accounted for. The presence of tilt may cause a fragmentation pattern which appears to "fit" into the crystalline lens in a particular longitudinal sectional image, when in fact the pattern, extends outside the boundaries of the lens, i.e., the pattern would cut through the lens capsule when the full three dimensional shape of the tilted lens is taken into account.

Alternatively, in conventional laser cataract surgery, the longitudinal sectional image or images may be processed automatically to find the position of edges representing the curved anterior and posterior surfaces of the cornea and lens in a laser-defined coordinate system. Examples of such automatic processing can be found in U.S. Provisional Patent Applications Nos. 61/228,506 and 61/455,178 and U.S. Patent Application Publications Nos. 2010/0004641 and 2010/0022995, the entire contents of each of which is incorporated herein by reference. If numerical curve fitting is applied to the edge points corresponding to a particular one of the eye's four optical surfaces, for example using a RANSAC curve fitting algorithm, (see, Peihua Li and Xian-zhe Ma, "Robust Acoustic Source Localization with TDOA Based RANSAC Algorithm", in Emerging Intelligent Computing Technology and Applications, edited by De-Shuang Fluang et al, Springer-Verlag, Berlin, 2009), a mathematical representation of the position of the surface within the longitudinal sectional images can be found. By repeating the process, a two dimensional mathematical representation, in the form of an arc of a circle, of each of the four surfaces can be obtained as shown in FIG. 3. (It should be noted that the term "arc" is meant to mean a curve with a more or less constant radius of curvature. However, the arc may refer to a section of an ellipse, a small section of a parabola, etc., within our usage.) Although not shown, the pupil position could also be derived automatically from the longitudinal sectional image or from an image from a camera pointing at the eye and the capsulotomy be centered by the laser system at the center of the pupil.

The computer image processing and curve fitting mentioned previously improves on the manual method in that the positions of the anterior and posterior cornea and lens surfaces can be found more accurately and repeatably and a necessary safety margin between the laser fragmentation pattern and lens capsule can be imposed automatically and precisely by the software. Despite the advantages mentioned above, the method still suffers from the problem of lens tilt. In addition, both the manual and automatic versions of this method are subject to large errors due to lens tilt as explained below.

In the methods mentioned above, the position of the laser capsulotomy is still, of necessity, at the center of the pupil, with the limitations of that type of positioning. All the foregoing methods, which involve a single planar sectional image of the eye, suffer from the possibility that the lens is tilted with respect to the axis of the laser optics. There are still alternate methods, such as disclosed in U.S. Provisional Patent Applications Nos. 61/228,506 and 61/455,178 and U.S. Patent Application Publications Nos. 2010/0004641 and 2010/0022995, that utilize two or more longitudinal or nearly longitudinal sectional images of the eye to reconstruct limited 3D models of the eye, which suffer from the same problem of not explicitly accounting for lens tilt. Such tilting may be the result from a slightly off-center docking of the laser system to the eye. (The laser system must be "docked" to the eye to hold the eye stationary and in a known position and orientation with respect to the coordinate system of the laser and the laser's built in eye measuring system.) This is conventionally accomplished by placing a specially designed circular suction ring on the eye at or near the limbus. The suction ring is docked or fastened to the laser in a rigid, defined manner to hold the eye at a fixed position relative to the laser. As shown in FIGS. 4A-B, if the suction ring is applied asymmetrically, i.e. centered with respect to the center of the limbus, the eye will be held by the docking device at an angle, tilted with respect to the laser axis.

As schematically shown in FIGS. 5A-C, a three-dimensional shot pattern has been placed within a three-dimensional representation of the lens, based on a single longitudinal sectional image of the eye as shown in FIG. 5A. Note that in FIGS. 5A-C, the lens capsule surrounding the lens is shown in gray and the shot pattern in pink. As shown in FIG. 5A, the shot pattern appears to fit within the lens capsule in this view. However when the lens and the embedded shot pattern are rotated by 45° (FIG. 5B) or 90° (FIG. 5C) around the Z axis, it is apparent that the shot pattern does not completely fit within the lens capsule. Thus, basing the placement of the laser phaco fragmentation pattern on a single longitudinal sectional image of the eye can lead to errors in such placement. Thus, to ensure that the shot pattern completely fits within the lens capsule, it is necessary to know the three-dimensional geometry of the lens, and in particular, the amount with which the lens is tilted with respect to the axis of the laser and biometric system. Although not shown, a similar problem exists with the placement of a capsulotomy or LRI on the basis of a single longitudinal section image of the eye.

FIGS. 5A-C illustrate the general problem that in order to place laser incisions in the cornea, or cut a laser capsulotomy of minimal edge height, or to cut a laser phaco fragmentation pattern within the crystalline lens, the three-dimensional shape and position of the target tissue must be known. In order to address this problem, an accurate determination of the three-dimensional shape and position of target tissue and the tilt of the lens relative to laser and biometric system coordinate system need to be known in order to properly center the capsulotomy, position the laser phaco fragmentation pattern appropriately within the lens and place corneal incisions correctly within the cornea, leaving appropriate safety margins with respect to preventing damage to nearby tissue.

BRIEF SUMMARY

One aspect of the present invention regards a method of generating three dimensional shapes for a cornea and lens of an eye, the method including illuminating an eye with multiple sections of light and obtaining multiple sectional images of said eye based on said multiple sections of light. For each one of the obtained multiple sectional images, the following processes are performed:

a) automatically identifying arcs, in two-dimensional space, corresponding to anterior and posterior corneal and lens surfaces of the eye by image analysis and curve fitting of the one of the obtained multiple sectional images; and b) determining an intersection of lines ray traced back from the identified arcs in two-dimensional space with a known position of a section of space containing the section of light that generated the one of the obtained multiple 1 sectional images, wherein the determined intersection defines a three-dimensional arc curve. The method further including reconstructing three-dimensional shapes of the anterior and posterior cornea surfaces and the anterior and posterior lens surfaces based on fitting the three-dimensional arc curve to a three-dimensional shape.

A second aspect of the invention regards a method of surgically treating an eye that includes generating three dimensional shapes for a cornea and lens of an eye. The method of generating three dimensional shapes includes illuminating an eye with multiple sections of light and obtaining multiple sectional images of said eye based on said multiple sections of light. For each one of the obtained multiple sectional images, the following processes are performed:

a) automatically identifying arcs, in two-dimensional space, corresponding to anterior and posterior corneal and lens surfaces of the eye by image analysis and curve fitting of the one of the obtained multiple sectional images; and b) determining an intersection of lines ray traced back from the identified arcs in two-dimensional space with a known position of a section of space containing the section of light that generated the one of the obtained multiple 1 sectional images, wherein the determined intersection defines a three-dimensional arc curve. The method further including reconstructing three-dimensional shapes of the anterior and posterior cornea surfaces and the anterior and posterior lens surfaces based on fitting the three-dimensional arc curve to a three-dimensional shape. The method of surgically repairing an eye further includes forming cuts in the eye based on the reconstructed three-dimensional shapes of the cornea and the lens.

One or more aspects of the present invention allow for compensating for the angular orientation of the cornea and the lens of an eye.

BRIEF DESCRIPTION OF THE DRAWING

The accompanying drawings, which are incorporated herein and constitute part of this specification, and, together with the general description given above and the detailed description given below, serve to explain features of the present invention. In the drawings:

FIGS. 5A-C schematically show a three-dimensional shot pattern placed within a three-dimensional representation of the lens, based on a single longitudinal sectional image of the eye wherein FIGS. 5A-C represent different angular orientations of the lens with respect to the Z axis;

FIG. 6 schematically shows an embodiment of a process for reconstructing a three dimensional model of the cornea and crystalline lens in accordance with the present invention;

DETAILED DESCRIPTION OF THE PREFERRED EMBODIMENTS

In accordance with the present invention, when two or more longitudinal sectional images of the eye are obtained, the positions of an optical surface (anterior or posterior cornea or lens surface), as characterized mathematically for each longitudinal sectional image, can be used to generate a three dimensional model of the surface, by curve fitting the edge points found from each image to the mathematical representation of a sphere, using a least squares algorithm. The process is repeated to obtain the mathematical representations of each of the anterior or posterior cornea or lens surfaces in terms of a best-fit sphere or other appropriate mathematical representation of the surfaces, such as modeling the surfaces in a Zernike polynomial expansion.

Figure 7:
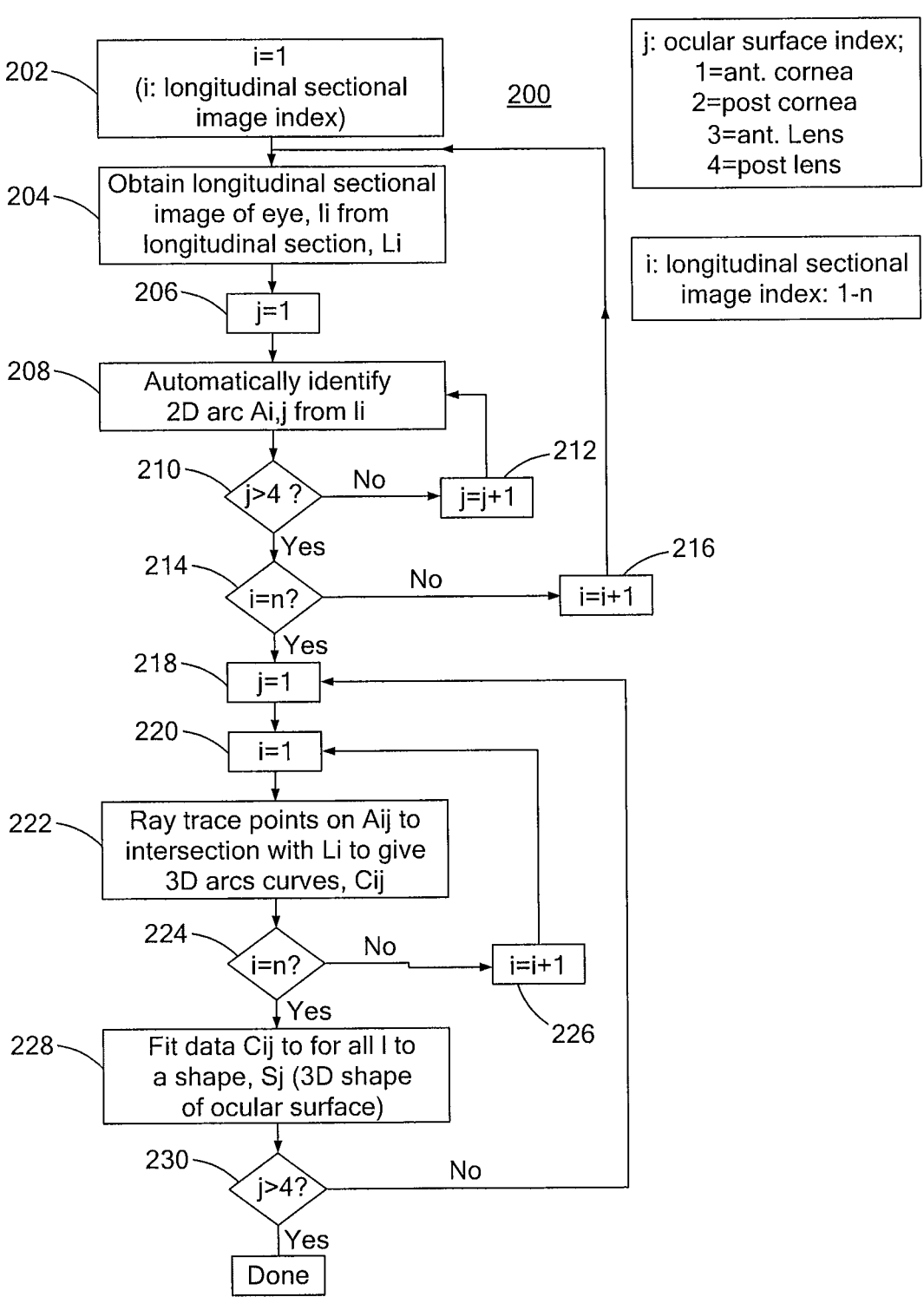
FIG. 7 shows a flow chart of the reconstruction process shown in FIG. 6.

A particular process 200 for reconstructing a three dimensional model of the cornea and crystalline lens within a coordinate system defined by the camera and laser is shown in FIGS. 6 and 7. In the case of FIG. 6, only a single longitudinal sectional image of the eye is shown for sim-
plicity sake. However, two or more longitudinal sectional
images are required to create a three dimensional shape for
the cornea and lens s in accordance with the present inven-
tion. As shown in FIG. 6, a longitudinal section of an eye is
illuminated by a longitudinal sheet of light 100, Lj, gener-
ated by a light source (not shown), such as described in U.S.
Provisional Patent Application Ser. No. 61/455,178. The
light 100 is scattered from the cornea and lens of the eye
back to a camera (not shown). A longitudinal sectional
image of the eye is obtained by the camera per process 204
of FIG. 7 and stored in a processor (not shown) that is in
communication with the camera.

Figure 1:
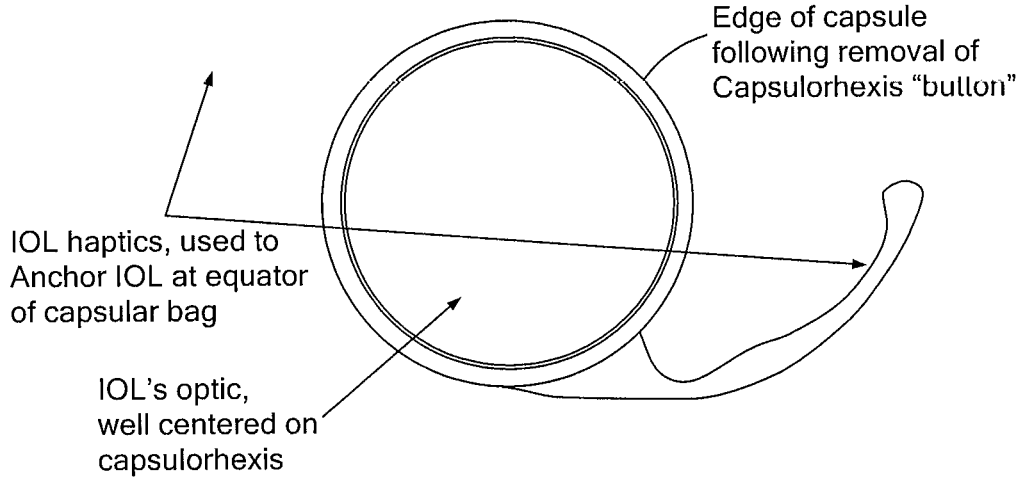
FIG. 1 shows an image of an IOL placed into a capsule so that the IOL's optic is centered on the capsulorhexis.
Figure 2:
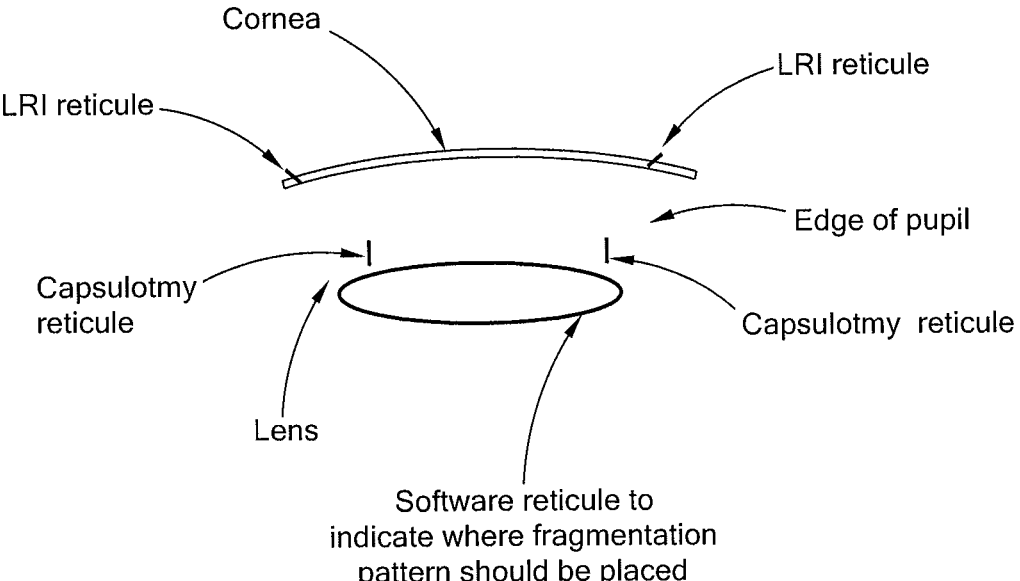
FIG. 2 shows an image of an eye with software reticules superimposed on the image.
Figure 3:
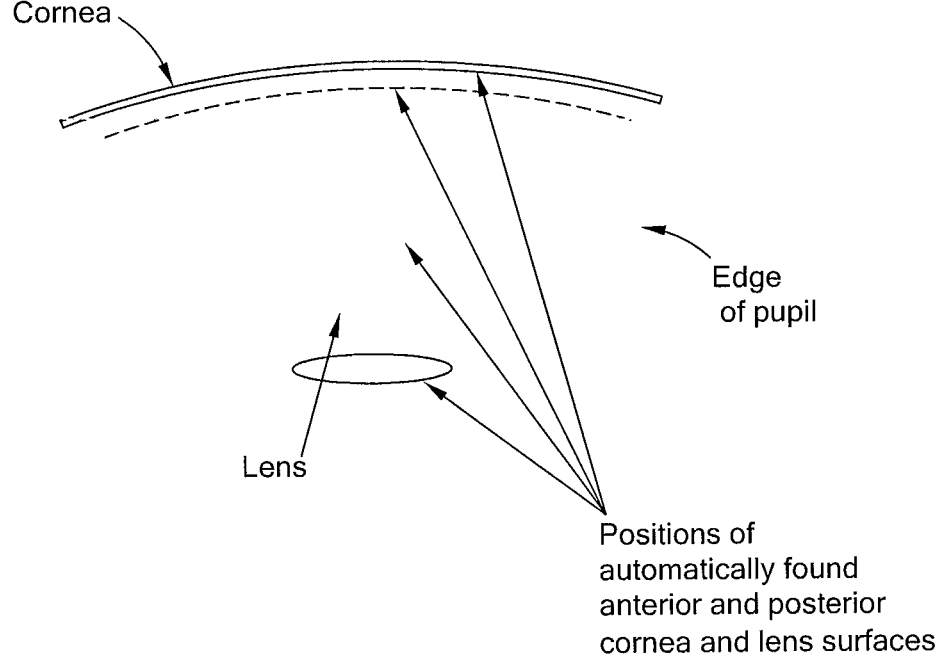
FIG. 3 shows an image of an eye with a two dimensional mathematical representations of the lens and corneal surfaces in the form of arcs of a circle superimposed on the longitudinal sectional image.
Figures 4A, 4B:
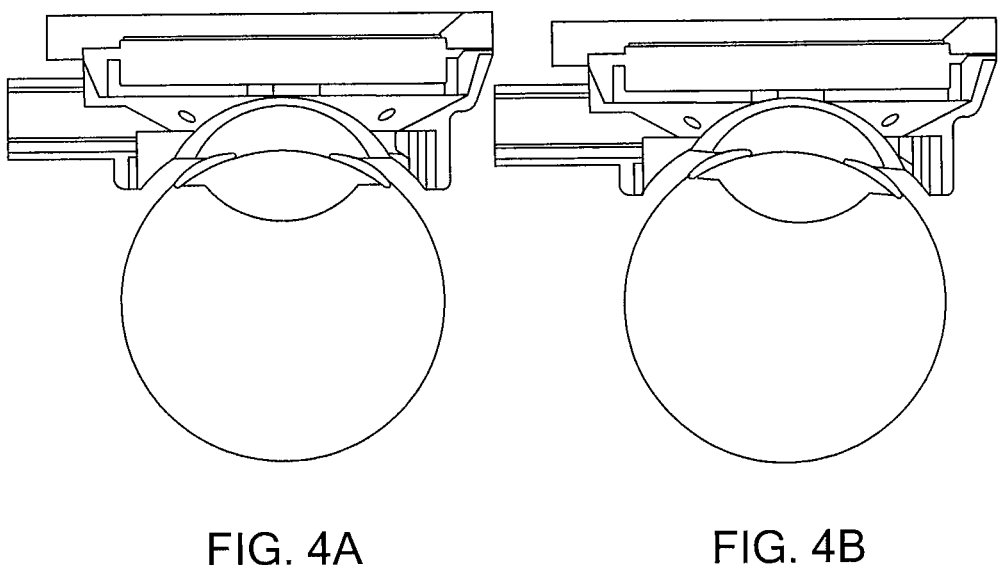
FIGS. 4A-B schematically show two different instances of where an eye is docked in place by a suction ring, wherein such docking results (A) in the eye being held without tilt and (B) an eye being held at an angle, tilted with respect to the laser axis.

Per processes 206, 208, 210 and 212 shown in FIG. 7, four
two-dimensional curves are automatically identified from
the obtained longitudinal sectional image by analysis and
curve fitting. The four curves are similar to the ones shown
in FIG. 3 in that two of them correspond to the posterior and
anterior surfaces of the cornea and the other two correspond
to the posterior and anterior surfaces of the crystalline lens.

The above process is repeated n−1 additional times per
processes 214, 216, etc., wherein n is >1. In other words, the
process is repeated for n−1 additional longitudinal sectional
images that are obtained per process 204. The end result is
that n sets of four two-dimensional curves are obtained,
wherein each curve is represented by the parameter Ay,
wherein i=1, . . . n and j=1, 2, 3, 4. Such curves Ay are stored
in a memory to be later processed by a processor.

Next, ray tracing is performed surface-by-surface starting
with the anterior surface of the cornea, j=1, per processes
218, 220 and 222. For the anterior surface of the cornea, ray
tracing is performed between each of the anterior surface
two-dimensional curves An (i=1, . . . n) in that rays that
begin from the image plane of the camera are traced to
follow their path as they pass through an ocular surface of
the eye where the ray is bent in accordance with SnelPs law.
Next, it is determined where such rays pass through the
longitudinal sectional light plane L;, that corresponds to the
curve An that is the subject of the ray tracing. (The anterior
corneal surface, because it is the most anterior ocular
surface, does not pass through any other ocular surfaces on
its way to the LjS, but rays from all the other ocular surfaces
refract through one or more ocular surfaces on their way to
the LjS.) The intersection of the rays with the plane, Lj,
results in defining a three-dimensional arc curve Qi in
three-dimensional space. Note that three-dimensional space
means the three dimensional volume of space occupied by
the eye being measured. This process is repeated for each of
the longitudinal sectional images, lj, and planes, Ll, wherein
i=1, . . . n. The curves $C_M$, i=1, . . . n are then fit to a
three-dimensional shape, Si, per process 228. Such fitting
involves using the curves Cil for i=T . . . n 1 to find the
shapes of the ocular surfaces, Si, based on finding the best
sphere (or other shapes like a Zernike polynomial expan-
sion) that simultaneously fits all the curves, Qi, from each
longitudinal section for corresponding to that ocular surface.

As shown in FIG. 7, the above-mentioned ray tracing and
fitting processes 222 and 228 are repeated for the other
surfaces, j=2, 3, 4, corresponding to the posterior surface of
the cornea Q=2), the anterior surface of the lens (j=3) and
the posterior surface of the lens (j=4). The three-dimensional
surfaces, Sj, j=1 . . . 4, represent a mathematical model of the
eye in the exact three-dimensional volume of space occupied
by the real eye in a three-dimensional coordinate system
defined by the laser and the camera system.

Note that in the case where the anterior and posterior
cornea and lens surfaces were modeled as spheres, two longitudinal section images would suffice for reconstruction
of the three-dimensional shape of the cornea and lens. If
more than two longitudinal section images are obtained and
process, a more accurate reconstruction of the three-dimen-
sional geometry will result. Alternatively, the two or more
longitudinal surfaces could be used with other three-dimen-
sional geometries, such as those described by Zernike poly-
nomials (see, Chapter 26, "Zernike Polynomials", in *The
Handbook of Formulas and Tables for Signal Processing*,
Ed. Alexander Poularikas, CRC Press, Boca Raton, 1999)
that are commonly used in ophthalmology to describe lens
and corneal refractive properties, to reconstruct the cornea
and lens surfaces.

Figure 8:
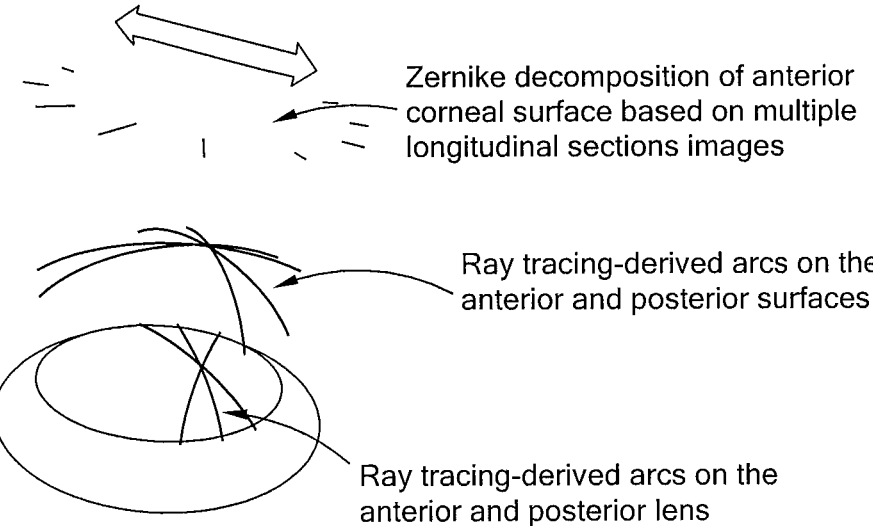
FIG. 8 shows a process for reconstructing a three dimensional model of the cornea and crystalline lens using multiple sectional images in accordance with the present invention, wherein the anterior corneal surface has been modeled in two ways: as a spherical surface and (above) as a surface defined at a Zernike polynomial expansion.

FIG. 8 shows the reconstruction of anterior and posterior
corneal and lens modeled spherical surfaces per process 200
derived from multiple longitudinal sectional images of the
eye and using the automatic image and numerical analysis of
the images to identify the two-dimensional arc surfaces and
ray tracing to find the three-dimensional coordinate points
along the arcs of the corneal and lens surfaces in the
laser/biometric system coordinates. A Zernike decomposi-
tion of the anterior cornea surface, using the same data is
also shown.

Note that FIG. 8 is intended to show how three-dimen-
sional models of the anterior and posterior cornea and lens
surfaces could be reconstructed using images created by a
longitudinal plane of light and an off axis camera, for
example, a Scheimpflug camera. Similar processes would be
followed with longitudinal sectional images obtained from
an Optical Coherence Tomography (OCT). In this case, the
ray tracing process would not be needed Instead, the previ-
ously mentioned two dimensional arcs, Ay, are transformed
directly into the three-dimensional space curves, Cy by
scaling the coordinate system of the longitudinal sectional
images, to the scale scanned three dimensional volume in the
eye. Otherwise the OCT method is equivalent to what was
previously described with respect to FIGS. 6-7.

Explained in another way, the z positions of points along
the arcuate shapes of the anterior and posterior cornea and
lens surfaces in the OCT images would be derived from the
time or frequency domain information inherent in the OCT
measurement method; and the x and y coordinates would be
taken from the known position and pointing direction of the
OCT scan, relative to the coordinate system of the OCT and
laser. Once the coordinates in either 1) the OCT and laser
coordinate system or 2) a mathematical description of the
coordinates for a number of points on the anterior and
posterior cornea and lens surfaces are known, two or more
non-coincident scans are sufficient to model the surfaces as
spheres. (By non-coincident is meant that the scans pass
through the eye oriented such that the illuminated longitu-
dinal sectional scans must intersect each other at a dihedral
angle that is non-zero. Ideally, for a two scan reconstruction,
the longitudinal sectional scans would be perpendicular to
each other. For more than two scans, it is efficient to have the
scans rotated at equal angles about the optical axis of the
eye. If the longitudinal sections that are parallel to each other
are used, they should be spaced out across the diameter of
the eye. For example, four scans might be disposed such that
the scans would intersect a cross section of the eye in the
form a "tic tac toe" pattern. The important point is to sample
as much of a cross section of the eye as possible.) Again,
more than two coincident scans would allow for a more
accurate reconstruction of the three-dimensional geometry.
Similarly, analogous to the example above, if more than
three longitudinal surfaces are used, three-dimensional
geometries of more complex surfaces such as those described by Zernike polynomials could be derived for the cornea and lens surfaces. OCT allows the capability of making non-planar scans, such as circular scans that generate cylindrical sections of the eye.

The three-dimensional anterior and posterior cornea and lens surface models could be equally derived from various sorts of non-planar scans. One example would be making a series of concentric cylindrical sections of the eye and deriving models of the anterior and posterior cornea and lens surfaces from these sections. A single spiral scan would also provide sufficient information about the cornea and lens surfaces to create accurate complex geometrical models of the surfaces. Again, the guiding principal of the selection of the illuminated sections is that the intersection of these vertical sections, regardless of shape, with a cross section of the eye covers the cross section as much as possible. This provides the maximum amount of information to accurately reconstruct the three dimensional shapes of the ocular surfaces.

In any of the methods detailed in this description, mathematical three-dimensional models of the anterior and posterior cornea and lens surfaces are found. The position of the pupil of the eye can also be found. The three-dimensional models can be used to correctly center the capsulotomy on an optical axis of the eye. This can be done in a number of ways. If spherical three-dimensional models are used, each spherical surface will be described in terms of four parameters: 1) the radius of curvature of the sphere and 2-4) the three coordinates of the center of curvature of the sphere. In an ideal eye, all four centers of curvature would fall along a line, which is the optic axis of the eye. However, in real eyes, the centers of curvature may fall slightly off a single line and the best estimate of the optical axis of the eye would be a line passing as close as possible through all four centers of curvature, determined, for example by a least squares fit of a line to the four centers of curvature. The intersection of that line with the anterior cornea would provide the target center of the laser capsulotomy. If such a capsulotomy centration process were used, and if the IOL were placed centered on the capsulotomy, the optic axis of the eye would be generally preserved and aberrations due to misalignment of the IOL axis with the corneal axis would be minimized.

It is occasionally the case that the imaging data is not of sufficiently high quality that the center of curvature of one or more of the lens or cornea surfaces can be determined accurately. This problem occurs more often with the posterior lens surface because of the need to measure this surface through the other surfaces and through the obscuring properties of the cataract. In this case, the best estimate of the optical axis of the eye would be found using the surfaces for which data of sufficient quality was available. As long as two or more centers of curvature were available, with at least one from a lens surface, a reasonably accurate estimate of the optic axis of the eye is possible. (The two corneal centers of curvature are generally so close together that defining the optic axis of the eye with just these two points is not sufficiently accurate.)

For most eyes, the central circular region of diameter 5-6 mm closely follows a spherical shape and the use of spherical models is easy and convenient, other three-dimensional geometrical forms for the corneal and lens surfaces can be utilized. If other geometrical forms are used, such as three dimensional surfaces based on Zernike polynomials or their equivalent, an equivalent for that geometrical form of center of curvature of the sphere must be used in place of the center of curvature of the sphere. With this substitution, the foregoing method can still be followed.

Once the choice for the center of the capsulotomy is made, the intersection of a cylinder of the diameter of the capsulotomy, and centered on the chosen optical axis of the eye, with the anterior capsule surface provides the three-dimensional trajectory of the ideal laser capsulotomy pattern. In general if the eye is docked with some de-centration, the ideal capsulotomy will be tilted with respect to the plane perpendicular to the axis of the laser. If the lens is not radially symmetric, the three-dimensional trajectory may be even more complex. The beam guidance system of the laser should follow the three-dimensional trajectory of the ideal capsulotomy pattern. When this process is followed, the edge height of the capsulotomy can be very small with the advantages described previously.

The three-dimensional models of the anterior and posterior cornea and lens surfaces also provide a way to optimize the laser phaco fragmentation pattern within the boundaries of the lens capsule, even if the eye is tilted with respect to the laser axis. If a fragmentation pattern of a particular geometry is desired, for example pies and cylinders, a series of concentric cylinders, intersected by a series of radial "blades", the pattern can be customized to fit within the boundaries of the lens. Generally, the pattern is centered on the pupil, which can be found with an analysis of multiple longitudinal sectional images or by a separate camera of know position and pointing direction within the laser/biometric system coordinate system. The pattern must be within the pupil because the lasers cannot cut behind the iris without damaging it. A small safety margin (0.1-0.5 mm) is generally incorporated to avoid hitting the pupil; thus the fragmentation pattern diameter will be no greater than the diameter of the pupil less the safety margin. The three-dimensional geometry of the anterior and posterior cornea and lens surfaces can be used to constrain the anterior and posterior extent of the pattern; again a safety margin of 0.25 to 1 mm is needed to allow for imprecision in the biometric measurements and for laser pointing inaccuracies.

Other types of laser phaco fragmentation patterns can be customized to fit within the boundaries of the capsule, as above, leaving the minimal safe margin between the outermost extent of the pattern and the lens capsule in order to allow fragmentation of as much of the lens as possible, for reasons described above.

Corneal incisions are defined in an analogous way. The LRI (limbal relaxing incisions) or AK (astigmatic keratotomy) incisions are arcuate incisions generally placed in diametrically disposed pairs, with the angular subtend of the arcs (usually 30 to) 90° chosen by the amount of astigmatic correction required. The depths of the incisions are generally 80-90% of the thickness of the cornea at the locations of the incisions. Since the corneal thickness is not uniform, the determination of the positions of particularly the posterior corneal surface is important. The ideal trajectory of the laser in cutting the LRI or AK incision should follow the shape of the posterior cornea at a distance starting at the desired residual corneal thickness above the posterior corneal surface.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A laser system for cutting an eye, the system comprising:

a biometric system;

the biometric system configured for generating three dimensional shapes for a cornea and lens of an eye, the biometric system comprising:

(a) an illumination source configured to direct multiple sections of light to an eye;

(b) a camera, configured to receive multiple sectional images of the eye generated by the multiple sections of light;

(c) an image processor system in communication with the camera; and, (d) the image process system configured to perform the following processes on an obtained sectional image:

(i) identifying arcs, in two-dimensional space, corresponding to anterior and posterior corneal and lens surfaces of the eye from the obtained sectional image by image analysis and curve fitting of the obtained sectional image;

(ii) determining an intersection of lines ray traced back from the identified arcs in two-dimensional space from one of the obtained multiple sectional images to an intersection of the lines with a known position of a section of space containing the section of light that generated the one of the obtained multiple sectional images, wherein the determined intersection defines a three-dimensional arc curve; and (iii) determining coordinates of arcs of the one of the multiple sectional images based on the one of the multiple sectional images and the determining an intersection of lines; and (iv) reconstructing three-dimensional shapes of the anterior and posterior cornea surfaces and the anterior and posterior lens surfaces based on fitting the three-dimensional arc curve to a three-dimensional shape;

wherein the laser system is configured to form a cut in the eye based at least in part on the reconstructed three-dimensional shape of the lens.

2. The system of claim 1, wherein the laser system is configured to form a cut in the eye based at least in part on the reconstructed three-dimensional shape of the cornea.

3. The system of claim 1 or 2, wherein the cut comprises a capsulotomy.

4. The system of claim 1, wherein the cut comprises a capsulotomy and wherein the system is configured to center the capsulotomy based at least in part on the reconstructed three-dimensional shape of the lens.

5. The system of claim 2, wherein the system is configured to center the capsulotomy based at least in part on the reconstructed three-dimensional shape of the lens and the cornea.

6. The system of claim 1, wherein the cut comprises a capsulotomy and wherein the system is configured to center the capsulotomy, wherein the centering comprises:

(a) finding three-dimensional models for determining centers of curvature for at least two of the anterior and posterior cornea and lens surfaces;

(b) calculating a line from coordinates of the determined centers of curvature; determining a point where the line intersects the anterior cornea surface; and centering an IOL on the capsulotomy based on the determined point.

7. The system of claim 6, wherein the three dimensional models are spherical three dimensional models.

8. The system of claim 6, wherein the three dimensional models are three dimensional surfaces based on Zernike polynomials or their equivalent.

9. The system of claim 1 or 2, wherein the section of light is a longitudinal sheet of light.

10. The system of claim 1 or 2, wherein at least one of the sections of light is non-planar.

11. The system of claim 1, wherein at least one of the sections of light is cylindrical.

12. The system of claim 1, wherein at least one of the sections of light is generated by a spiral scan.

* * * * *